(12) United States Patent  (10) Patent No.: US 8,221,861 B2
Keady  (45) Date of Patent: Jul. 17, 2012

(54) EARGUARD SEALING SYSTEM II: SINGLE-CHAMBER SYSTEMS

(75) Inventor: John P. Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 1032 days.

(21) Appl. No.: 12/115,364

(22) Filed: May 5, 2008

(65) Prior Publication Data

US 2008/0311324 A1    Dec. 18, 2008

Related U.S. Application Data

(60) Provisional application No. 60/916,275, filed on May 4, 2007.

(51) Int. Cl.
  *B32B 1/04*  (2006.01)
  *A61F 11/08*  (2006.01)
(52) U.S. Cl. ........................ 428/35.7; 181/135
(58) Field of Classification Search .......... 428/35.7, 428/34.1; 181/135
  See application file for complete search history.

(56) References Cited

U.S. PATENT DOCUMENTS

| | | | |
|---|---|---|---|
| 2,535,258 A | 12/1950 | Bland | |
| 3,110,356 A * | 11/1963 | Mendelson | ............ 181/130 |
| 3,602,654 A | 8/1971 | Victoreen | |
| 3,987,245 A | 10/1976 | Fasen | |
| 4,732,930 A | 3/1988 | Tanaka | |
| 4,741,344 A | 5/1988 | Danby et al. | |
| 4,834,211 A | 5/1989 | Bibby et al. | |
| 4,896,679 A | 1/1990 | St. Pierre | |
| 4,962,537 A | 10/1990 | Basel et al. | |
| 5,107,852 A * | 4/1992 | Davidson et al. | ............ 600/585 |
| 5,213,580 A | 5/1993 | Slepian | |
| 5,252,318 A | 10/1993 | Joshi | |
| 5,256,765 A | 10/1993 | Leong | |
| 5,333,622 A | 8/1994 | Casali et al. | |
| 5,410,016 A | 4/1995 | Hubbell | |
| 5,483,027 A | 1/1996 | Krause | |
| 5,514,379 A | 5/1996 | Weissleder | |
| 5,525,334 A | 6/1996 | Ito | |
| 5,575,815 A | 11/1996 | Slepian | |
| 5,589,568 A | 12/1996 | Higashijima | |
| 5,634,946 A | 6/1997 | Slepian | |
| 5,662,609 A | 9/1997 | Slepian | |
| 5,674,287 A | 10/1997 | Slepian | |
| 5,695,480 A | 12/1997 | Evans | |
| 5,702,361 A | 12/1997 | Evans | |
| 5,749,922 A | 5/1998 | Slepian | |
| 5,766,704 A | 6/1998 | Allen | |
| 5,843,156 A | 12/1998 | Slepian | |

(Continued)

*Primary Examiner* — Rena Dye
*Assistant Examiner* — Erik Kashnikow
(74) *Attorney, Agent, or Firm* — RatnerPrestia

(57) ABSTRACT

Single-chamber coatings are provided. The single-chamber coating includes a first medium, a second medium, and a ridge structure. The first medium covers at least a first portion of the second medium so as to form a chamber. At least one material property of the first medium is different than the second medium. The first medium forms a first wall of the chamber. The first wall is configured to apply a restorative force upon deformation of the chamber. The ridge structure is along a second wall of the chamber and is configured to direct the second medium substantially parallel to a ridge structure plane when the chamber is deformed. The chamber forms at least a portion of a coating. The coating is configured to be attached to an object that is configured to be inserted into an orifice.

12 Claims, 4 Drawing Sheets

U.S. PATENT DOCUMENTS

| | | | |
|---|---|---|---|
| 5,858,746 | A | 1/1999 | Hubbell |
| 5,876,741 | A | 3/1999 | Ron |
| 5,939,485 | A | 8/1999 | Bromberg |
| 5,942,209 | A | 8/1999 | Leavitt |
| 5,976,648 | A | 11/1999 | Li |
| 6,090,911 | A | 7/2000 | Petka |
| 6,094,494 | A | 7/2000 | Haroldson |
| 6,113,629 | A | 9/2000 | Ken |
| 6,256,396 | B1 | 7/2001 | Cushman |
| 6,339,648 | B1 | 1/2002 | McIntosh et al. |
| 6,352,682 | B2 | 3/2002 | Leavitt |
| 6,393,130 | B1 | 5/2002 | Stonikas et al. |
| 6,439,556 | B1 * | 8/2002 | Baudendistel et al. .. 267/140.15 |
| 6,451,429 | B2 | 9/2002 | Mumick |
| 6,660,247 | B1 | 12/2003 | Gutowska |
| 6,671,381 | B1 | 12/2003 | Lux-Wellenhof |
| 6,731,772 | B1 * | 5/2004 | Byun ............................ 381/380 |
| 7,130,437 | B2 | 10/2006 | Stonikas et al. |
| 7,164,775 | B2 | 1/2007 | Meyer et al. |
| 7,227,968 | B2 | 6/2007 | van Halteren et al. |
| 7,362,875 | B2 | 4/2008 | Saxton et al. |
| 7,387,187 | B2 | 6/2008 | Widmer et al. |
| 2002/0168319 | A1 | 11/2002 | Filler |
| 2004/0165742 | A1 * | 8/2004 | Shennib et al. ................ 381/326 |
| 2006/0159298 | A1 | 7/2006 | von Dombrowski et al. |
| 2006/0264897 | A1 * | 11/2006 | Lobl et al. ...................... 604/506 |
| 2007/0116319 | A1 | 5/2007 | Hagberg |
| 2008/0144871 | A1 | 6/2008 | Purcell et al. |
| 2009/0173353 | A1 | 7/2009 | Purcell et al. |
| 2009/0320858 | A1 | 12/2009 | Purcell et al. |
| 2009/0320859 | A1 | 12/2009 | Purcell et al. |

* cited by examiner

US 8,221,861 B2

EARGUARD SEALING SYSTEM II: SINGLE-CHAMBER SYSTEMS

CROSS-REFERENCE TO RELATED APPLICATIONS

This application claims the benefit of U.S. provisional patent application No. 60/916,275 filed on 4 May 2007. The disclosure of which is incorporated herein by reference in its entirety.

FIELD OF THE INVENTION

The present invention relates to chambered material configuration useable in orifices or as coatings for objects to be inserted into orifices, and more particularly though not exclusively for chambered material configurations used in organic orifices.

BACKGROUND OF THE INVENTION

Various methods of sealing an orifice, or coating a device to insert into an orifice (organic and non-organic) have been developed. Generally the coatings and sealing mechanism use simple flanges, single layer coatings, or layered coatings. All have various disadvantages in tactile response, comfort, and sealing ability.

SUMMARY OF THE INVENTION

At least one exemplary embodiment is directed to a single-chamber coating comprising: a first medium; a second medium; and a ridge structure, where the first medium covers at least a first portion of the second medium so as to form a first chamber, where at least one material property of the first medium is different than the second medium, where the first medium forms a first wall of the first chamber, where the first wall is configured to apply a restorative force upon deformation of the first chamber, where the ridge structure is along a second wall of the first chamber, where the ridge structure is configured to direct the second medium substantially parallel to a ridge structure plane when the first chamber is deformed, where the first chamber forms at least a portion of a coating, and where the coating is configured to be attached to an object that is configured to be inserted into an orifice.

At least one exemplary embodiment is directed to a sealing section comprising: a central core; and a single chamber coating, where the single-chamber coating is attached to the central core forming a sealing section, where the sealing section's length is less than 30 mm, and where the largest diameter along the sealing section's length is less than 20 mm, where the coating comprises: a first medium; a second medium; and a ridge structure, where the first medium covers at least a first portion of the second medium so as to form a first chamber, where at least one material property of the first medium is different than the second medium, where the first medium forms a first wall of the first chamber, where the first wall is configured to apply a restorative force upon deformation of the first chamber, where the ridge structure is along a second wall of the first chamber, where the ridge structure is configured to direct the second medium substantially parallel to a ridge structure plane when the first chamber is deformed, where the first chamber forms at least a portion of a coating.

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limited the scope of the invention.

BRIEF DESCRIPTION OF THE DRAWINGS

Exemplary embodiments of the present invention will become more fully understood from the detailed description and the accompanying drawings, wherein.

DETAILED DESCRIPTION OF EXEMPLARY EMBODIMENTS OF THE PRESENT INVENTION

Figure 1:
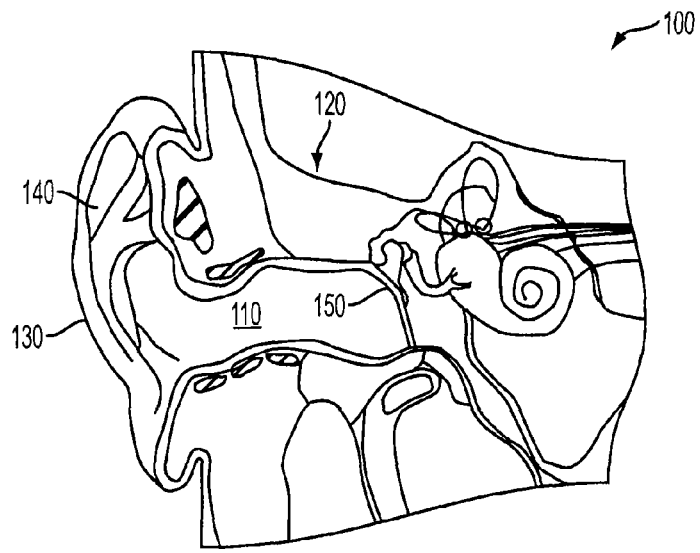
FIG. 1 illustrates an example of an orifice (e.g., ear)

The following description of exemplary embodiment(s) is merely illustrative in nature and is in no way intended to limit the invention, its application, or uses.

Exemplary embodiments are directed to or can be operatively used on various wired or wireless earpieces devices (e.g., earbuds, headphones, ear terminal, behind the ear devices or other acoustic devices as known by one of ordinary skill, and equivalents).

Note that medium can refer to any medium mentioned below and its equivalent as well as fluids (air, liquid, foams, gels, solids, electro active polymers and other materials as known by one of ordinary skill in the arts that can be used in coatings and fillers). Additionally the coatings can be used on any object not just those inserted into orifices (e.g., ear canals, blood vessels, pipes, irregular shaped cross-sectional openings, non-circular cross sectional openings).

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally exemplary embodiments are not limited to earpieces, for example some functionality can be implemented on other systems with speakers and/or microphones for example computer systems, PDAs, Blackberry™ Smartphones, cell and mobile phones, and any other device that emits or measures acoustic energy. Additionally, exemplary embodiments can be used with digital and non-digital acoustic systems. Additionally various receivers and microphones can be used, for example MEMs transducers, diaphragm transducers, for example Knowles' FG and EG series transducers.

Notice that similar reference numerals and letters refer to similar items in the following figures, and thus once an item is defined in one figure, it may not be discussed or further defined in the following figures.

Additionally, the size of structures used in exemplary embodiments are not limited by any discussion herein (e.g., the sizes of structures can be macro (centimeter, meter size), micro (micro meter), nanometer size and smaller).

Various materials are useable in exemplary embodiments. For example material referred to herein can be viscous and can include silicone-based polymers, gels, vinyl elastomers, or any other material of sufficient properties to allow the deformation of a membrane cavity from user contact. Materials can also be used to provide a slow reformation of the original membrane cavity shape after it has been deformed and released. In this regard, a silicone gel or other non-cross-linked polymer or uncatalyzed materials can be used. It should be appreciated that the composition of the fillable (e.g., material used in the cavity or chamber) material could be altered for applications in which varied membrane characteristics are desired (i.e. more stiffness, durability, more or less deformability and/or longer-lasting deformation). The fillable material may be elastically deformed or it may be deformed by displacement, which is the actual movement or flow of the fillable material in response to pressure, such as that from a user's fingertips. In addition, the fillable material could be altered for applications in which varied temperature conditions would be encountered during the use of particular products on which the membrane cavity is mounted.

Membranes can be made of any material, rigid or elastic, including various plastic or metal materials, or it can be made of a membrane formed of thin rubber-based material, deformable plastic or silicone-based materials or other elastomeric materials suitable for a given application. If the base is configured as a flexible membrane, the cavity (e.g., chamber covered by an outer membrane) can more easily conform to a product's surface, thereby increasing the ease with which the cavity can be installed, removed, and replaced. Likewise, the outer membrane also can be made of a thin rubber-based material, deformable plastic or silicone polymer materials, or other elastomeric materials suitable for a given application. If the base membrane and outer membrane are made of silicone material, both should be from 0.50 mm to 2.5 mm in thickness. In this regard, the base may be a membrane instead of a piece of rigid material. The edges of the outer membrane and the base membrane can be mechanically fastened or clamped forming the membrane cavity. Additionally at least a portion of the base membrane can be adhesively attached (e.g., adhesive tape, glue) or mechanically fastened to the support structure.

In applications where the base membrane is attached to the support structure via an adhesive, various types of adhesives can be used depending on the type of product surface (i.e., support structure) and the type of base material used. For example, if the base membrane of the cavity is a silicone polymer, then cyanoacrylate glue or 3M Super Silicone brand sealant can be used. In another example, if the support structure is a thermoplastic material and the base membrane of the cavity is a polyethylene plastic material, then cyanoacrylate glue or 3M Super Silicone brand sealant can be used.

One type of adhesive that may be used is 3M brand Super silicone sealant, which is a one-component, paste-like material that cures to a tough, elastomeric solid when exposed to atmospheric moisture. This sealant will adhere to clean, bare, or painted metal, glass, non-oily wood, abraded rubber and many types of plastics. The sealant is a one-part vulcanizing silicone rubber type having the consistency of a non-sagging paste. It is made of 100% solids and has a net weight of approximately 8.3-8.7 pounds per gallon. This sealant is available in clear, white or black colors. The sealant can be extruded from an 0.125 inch orifice using a pressure of ninety pounds per square inch. Such extrusion results in a flow of approximately 350 gallons per minute.

The silicone sealant can be an acetoxy cure type. In particular, upon exposure to moisture, the silicone sealant will give off small amounts of acetic acid while the sealant cures. It is not recommended that the acetic acid vapors be inhaled. The sealant will cure in 24 hours and has a tack free time of 10-20 minutes at 77.degree. F. (25.degree. C.) with 50% relative humidity. The sealant's tensile strength is approximately 350 psi, its elongation property is 450%, and its hardness is approximately 25-30 Shore A. The sealant has temperature stability from −85.degree. F. to 450.degree. F. (−65.degree. C. to 232.degree. C.) and can withstand intermittent exposure to temperatures as high as 500.degree. F. (280.degree. C.). The sealant is believed to have good resistance to various weathering conditions, including UV radiation, rain, snow, etc, without hardening, cracking, or shrinking.

For optimum adhesion with the above adhesive, the support structure and the lower surface of the base membrane should be clean, dry, and free from oil, grease or other foreign material. If necessary, metal surfaces should be wiped with a non-oily solvent. Rubber surfaces should be abraded to promote adhesion. Depending on environmental conditions, the base and product surface should be joined within 5-10 minutes, before the tack-free time of the sealant passes.

Additional materials that can be used include more exotic materials, for example materials that are electro active. The sealing section (e.g., which can include the coating) can use various materials (e.g., viscosity varying polymers), for example polymers that are liquid at one temperature then gel at another, or switch between a gel and liquid with pH, current, pressure, or any other variation in energy, or any other similar material as known by one of ordinary skill in the relevant arts. For example the following is a non-limiting list of references that discuss materials that can be used: U.S. Pub. No. 2002/0168319; U.S. Pat. No. 6,660,247; U.S. Pat. No. 6,352,682; U.S. Pat. No. 6,113,629; U.S. Pat. No. 6,090,911; U.S. Pat. No. 5,976,648; U.S. Pat. No. 5,942,209; U.S. Pat. No. 5,939,485; U.S. Pat. No. 5,876,741; U.S. Pat. No. 5,858,746; U.S. Pat. No. 5,843,156; U.S. Pat. No. 5,766,704; U.S. Pat. No. 5,749,922; U.S. Pat. No. 5,702,361; U.S. Pat. No. 5,695,480; U.S. Pat. No. 5,674,287; U.S. Pat. No. 5,662,609; U.S. Pat. No. 5,634,946; U.S. Pat. No. 5,589,568; U.S. Pat. No. 5,575,815; U.S. Pat. No. 5,525,334; U.S. Pat. No. 5,514,379; U.S. Pat. No. 5,410,016; U.S. Pat. No. 5,256,765; U.S. Pat. No. 5,252,318; U.S. Pat. No. 5,213,580; U.S. Pat. No. 6,660,247; and U.S. Pat. No. 4,732,930. Additionally electro-active polymers can be utilized. For example gels that expand and contract when an electric field is applied, likewise materials can bend and deform when voltage is applied across its surface.

The device can include a sealing section having a coating, that can be made of various materials, for example viscosity variable polymers, or temperature variable viscosity materials. As the device is inserted into an orifice (e.g., ear, mouth, anus, nose, artery, vein) a resistance force can be encountered by a portion of the sealing section. The force can act as an energy variation event which can change the physical properties, for example liquefies (e.g., lowers the viscosity, could still be gel like) the fillable material allowing easy flow or deforms a deformable sealing section. As the impulse forces stop and stability sets in (net equilibrium force reduced) the portion of the sealing section that liquefied in response to a force gellifies seating the device. Note that a sealing section could be a chamber coating.

Note that in some materials there is a phase shift in the temporal response of the medium. For example when a force is applied there may be a 10 msec delay in the liquefaction (change in viscosity) of the sealing element's fillable material. For example U.S. Pat. No. 6,451,429 discusses a method to synthesize a temperature sensitive polymer, NiPAm polymers. U.S. Pat. No. 6,451,429 discusses a condensation reaction of an intermediate salt to form homopolymers, copolymers and terpolymers of N-isopropyl acrylamide (NiPAm) with acrylic acid and/or alkyl acrylates in a molten state, which is adaptable to a continuous reactive extrusion process. Binder compositions, water-dispersible products and thermoformable articles containing the NiPAm polymers are also disclosed. Additional non-limiting examples are pH/temperature sensitive linear terpolymers (poly(N-isopropylacrylamide-co-butylmethacrylate-co-acrylic acid).

Note that various materials have been discussed, in addition all forms of electroactive polymers can be used. For example electroactive polymers (EAPs) are touted as the basis for future artificial muscles. EAPs can be deformed repetitively by applying external voltage across the EAP, and they can quickly recover their original configuration upon reversing the polarity of the applied voltage. Some EAPs have a high load bearing capacity to mass ratio, short response time, and nearly linear deformation response with respect to applied voltage. Artificial muscle polymers can be formed from a conductive polymer doped with surfactant molecule or from an ionic polymer metal composite (IPMC). Doped electroactive polymers (EAPs) are conductive polymers (e.g., polypyrrole or polyanaline) doped with a surfactant (e.g., sodium dodecyl benzene sulfonate). IPMCs typically consist of perfluorsulfonate polymers that contain small proportions of sulfonic or carboxylc ionic functional groups. Nafion®, a polymer made by DuPont, is one example of a poly(tetrafluoroethylene) based ionomer. The outer surface region (less than a micrometer) of the polymer sheet is then impregnated with a conductive metal such as platinum or gold. The resulting EAP polymer can absorb water until its physical ability to expand is balanced by the affinity of water for the polymer-fixed ions and free counter ions. When an electrical field is applied across the EAP, the EAP deforms as a result of stresses generated by the movement of water and mobile positive ions in the polymer composite.

FIG. 1 illustrates the general physical arrangement of the ear region 100, including a pinna 130, ridge 140, outer ear region 120, inner ear canal (IEC) region 110 and the eardrum 150. At least one exemplary embodiment is related to an earphone inserted into the ear canal, where a portion of a sealant section acoustically seals an inner ear canal region 110.

Figure 2:
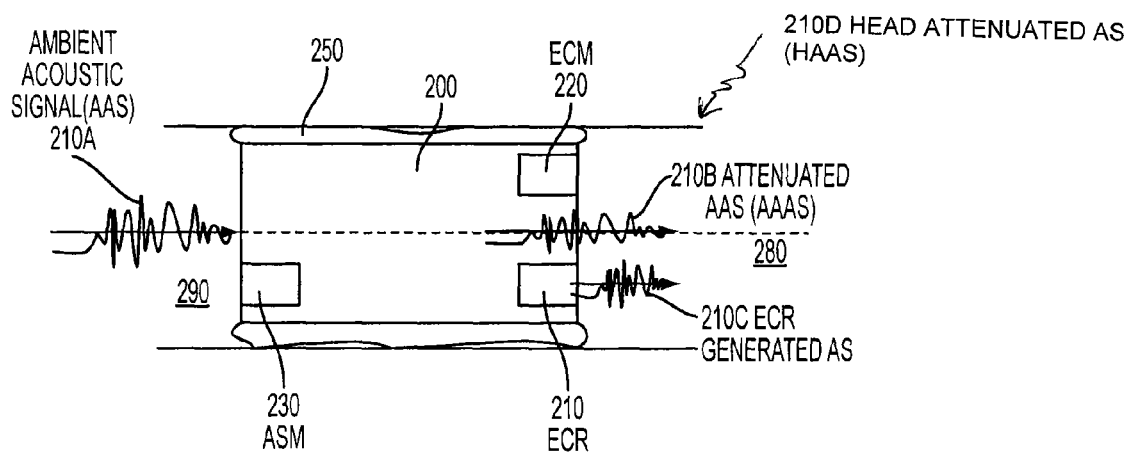
FIG. 2 illustrates an example of an object to insert into an orifice.

FIG. 2 illustrates a generalized version of an earpiece 200 and some associated parts (e.g., 230, 220, and 210) in an ear canal (EC) (an example of an orifice), which is a non limiting example of at least one orifice device (e.g., earpiece) which can contain a coating and/or layer 250 in accordance to at least one exemplary embodiment. When inserted the earpiece 200 generally defines the two regions 290 and 280. Through the earpiece 200 there is some attenuation. For example, an ambient acoustic signal (AAS) 210A, will travel through the earpiece 200 and/or via bone conduction (not shown) and be attenuated forming an attenuated ambient acoustic signal (AAAS) 210B. The AAAS 210B then travels to the eardrum (ED). The other additional acoustic signal 210C (e.g., the ECR generated AS or ECRAS), which can travel to the eardrum, can be generated by the ear canal receiver (ECR) 210. Thus the total AS imparting energy upon the ED can be due to the AAAS 210B (which can include a bone conduction part not in the IEC region 280) and the ECRAS 210C. Various combinations of elements (e.g., parts) can be used in exemplary embodiments such as the ECR 210 (e.g., Knowles FG3629), the ear canal microphone (ECM) 220 (e.g., Knowles FK3451), and the ambient signal microphone (ASM) 230 (e.g., Knowles FG3629). Note that ECM 220 can also measure head attenuated acoustic signals (HAAS) 210D, which for example could originate from voice.

During operation, a personal audio device outputs a driving signal to ECR 210 so that ECR 210 outputs an acoustic signal 210C. Similarly, ASM 230 converts the ambient environment noise into an environmental noise signal, which is input to ECR 210 to generate an ECR ambient sound acoustic signal, which could make up a part of acoustic signal 210C. ECM 220 receives an ambient acoustic signal AAS210B and the ECR-generated signal 210C and converts it into a total acoustic sound signal to be operated on by earpiece 200 as discussed below.

Figure 3:
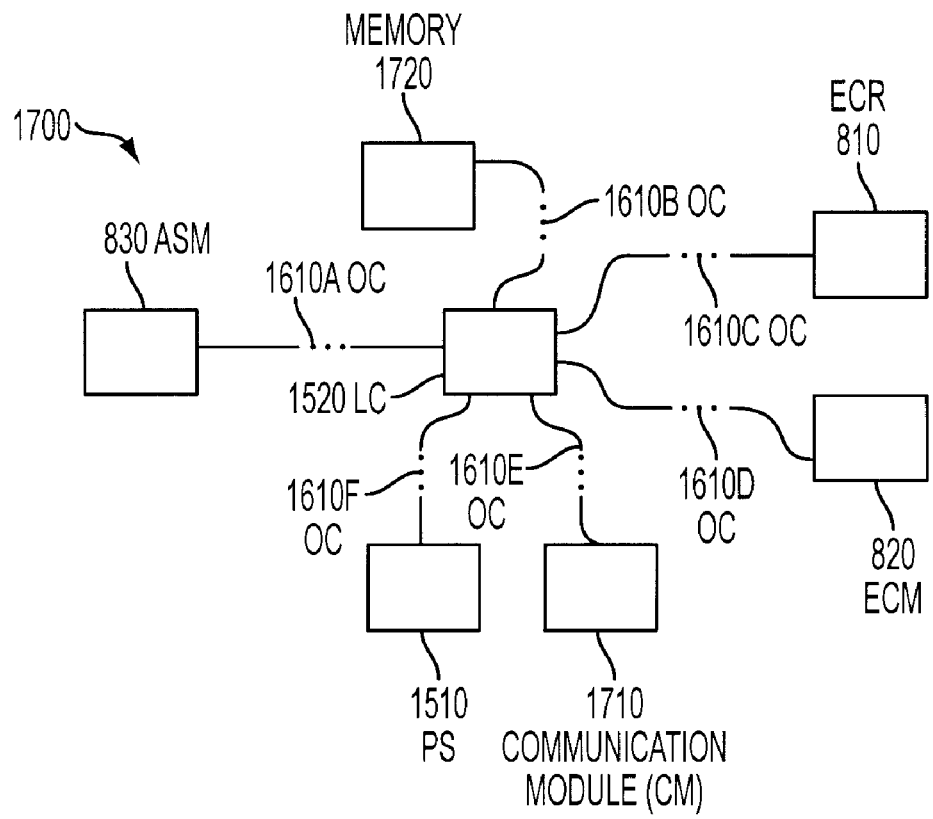
FIG. 3 illustrates a general configuration of electronic elements in an earpiece.

FIG. 3 illustrates a self-contained version of an earpiece 1700 according to at least one exemplary embodiment, including a power source (PS) 1510 (e.g., zinc-air battery (ZeniPower A675P), Li-ion battery), and a logic circuit (LC, e.g., Gennum Chip GA3280) 1520 in addition to ECR 810. Earpiece 1700 can also include a wireless module for wireless communications (not shown) or can be wired. Earpiece 1700 can also connect remotely to various parts (e.g., via a wired or wireless connection). As illustrated the LC 1520 and PS 1510 are operatively connected (OC) 1610 (e.g., via a wire or wirelessly) to the earpiece 1700. For example earpiece 1700 can be an earbud that includes ECR 810, whose signals travel back and forth via a wire that is operatively connected via a wire to LC 1520, which in turn can be operatively connected to PS 1510. Note that ECR 810 can also be a dual purpose ECR/ECM, where when the receiver function (ECR mode) is not used the microphone function (ECM mode) can be used. For example U.S. Pat. No. 3,987,245 discusses a dual-purpose transducer that can be used as a microphone and/or a receiver. Logic circuit 1520 has an operative connection 1610A to ASM 830; an operative connection 1610B to a memory 1720; an operative connection 1610C to ECR 810; an operative connection 1610D to ECM 820; an operative connection (e.g., operatively connected) 1610E to a communication module 1710; and an operative connection 1610F to a power source 1510. Again, it should be noted that the operative connection could be either wireless or hard wired and that as discussed above, elements other than ECR 810 could be remote from earpiece 1700. It should be understood that ASM 830 should not be too remote from the ear of the user in order to properly measure the ambient sound and ambient environment.

Figure 4:
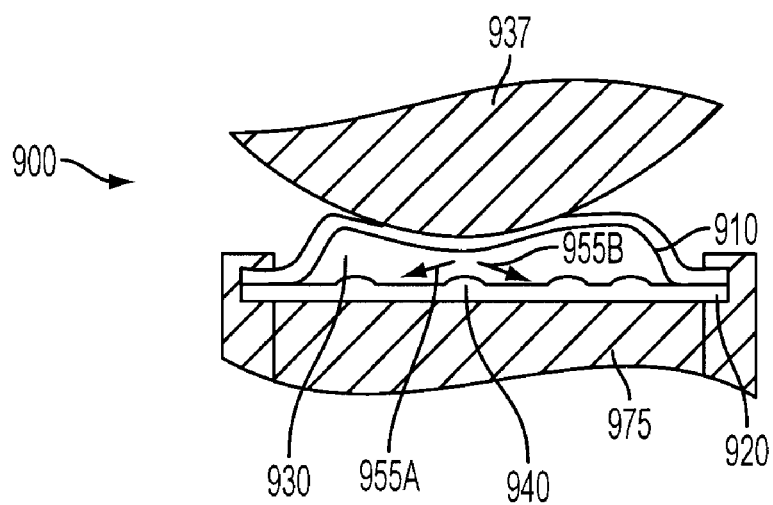
FIG. 4 illustrates at least one exemplary embodiment of a coating with a single chamber having ridges that can deflect deformed medium generally parallel to the plane to which the ridges are attached.

FIG. 4 illustrates a single chamber coating 900, having a first membrane 910 and a second membrane 920 (e.g., where 910 and 920 could include a first medium, and could be one membrane forming and enclosing a structure such as a bladder). The first and second membranes 910 and 920 can enclose or partially enclose a chamber 930 which can include a second medium. The first membrane 910, second membrane 920 and chamber 930 can comprise a coating 900. The coating can be attached to an object having a core 975 that can be inserted into an orifice (e.g., ear canal) where a wall of the orifice 937 deforms the coating 600. Upon deformation ridges 940 can direct the deformed second medium (depicted by arrows 955A and 955B) generally parallel to the plane of the ridges.

Figure 5A:
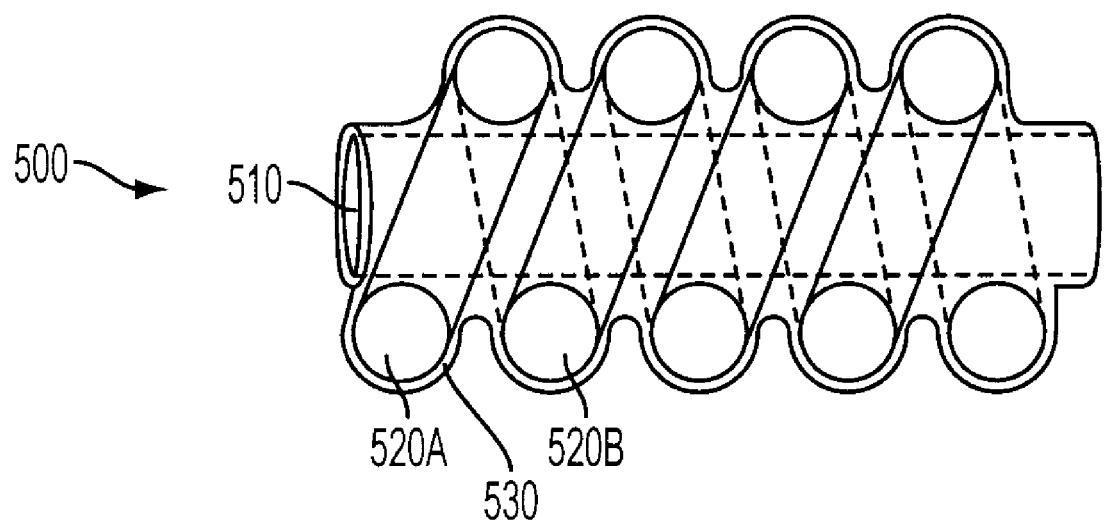
FIGS. 5A and 5B illustrates a single chamber coating where the single chamber can be wrapped around a central core in accordance with at least one exemplary embodiment.
Figure 5B:
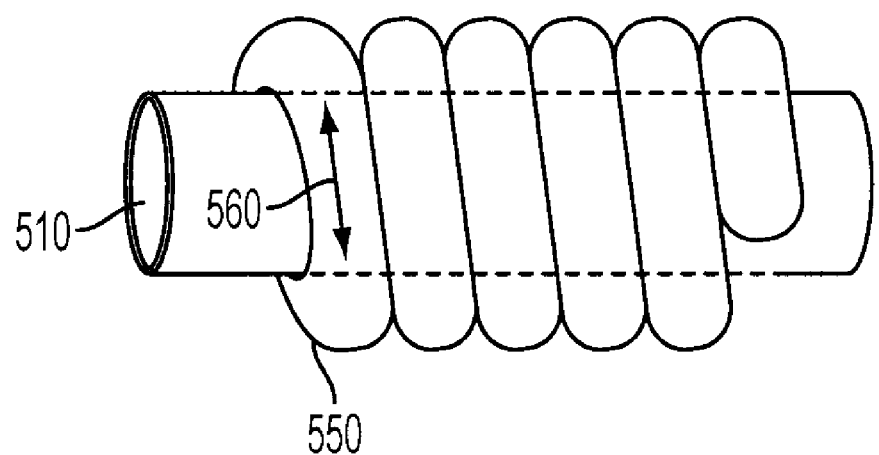

FIGS. 5A and 5B illustrate a single chamber coating 500 having a single chamber 550 that is wrapped around a central core 510. FIG. 5A illustrates the cross section 520A and 520B of the wrapped single chamber. The single chamber can be covered by a first medium 530. Note that a second medium in the single chamber can move (560) along the direction of the single chamber when deformed during insertion into an orifice. Note that although reference is made to a single chamber one can partition the single chamber in multiple chambers.

Figure 6:
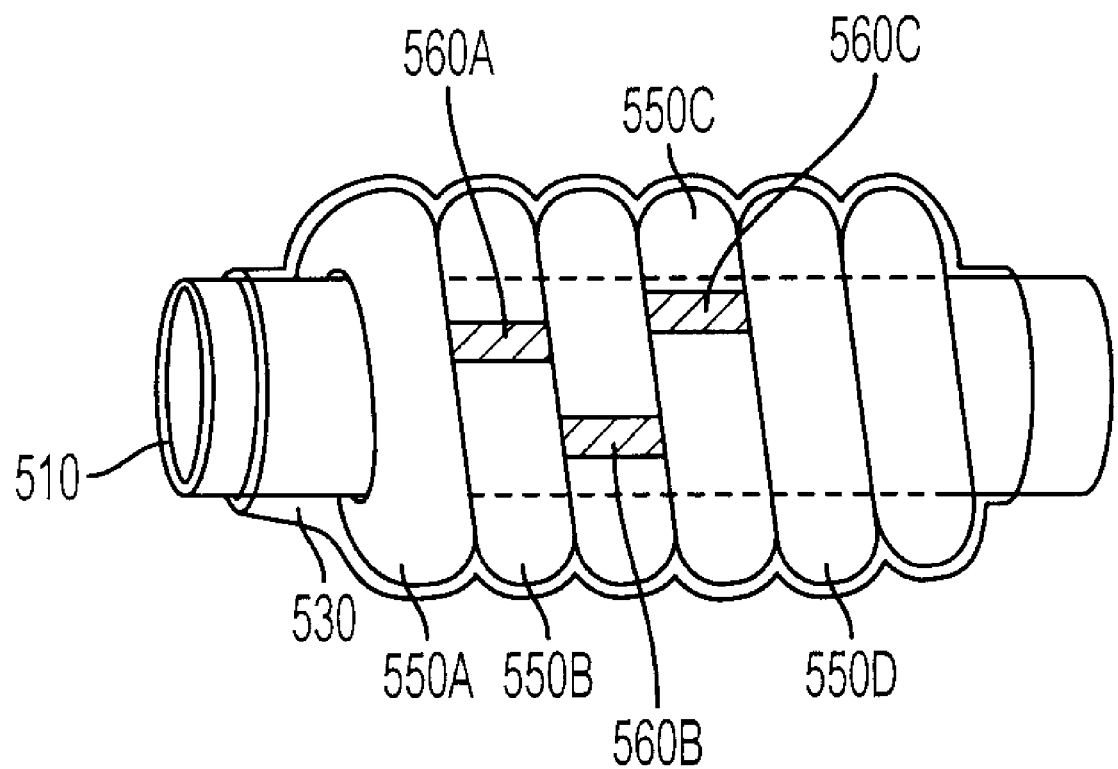
FIG. 6 illustrates a wrapped single chamber that has been partitioned into multiple chambers along its length.

For example FIG. 6 illustrates the spiral chamber of FIGS. 5A and 5B broken into sections (550A, 550B, 550C, 550D). Where the sections are separated by sections 560A, 560B, and 560C, which can be of a different material.

Note that although circular cross sections are illustrated, triangular, oval, square, irregular and regular cross sections can also be used and can vary as wrapped around a central core.

At least one exemplary embodiment is directed to a single-chamber coating comprising: a first medium; a second medium; and a ridge structure, where the first medium covers at least a first portion of the second medium so as to form a first chamber, where at least one material property of the first medium is different than the second medium, where the first medium forms a first wall of the first chamber, where the first wall is configured to apply a restorative force upon deformation of the first chamber, where the ridge structure is along a second wall of the first chamber, where the ridge structure is configured to direct the second medium substantially parallel to a ridge structure plane when the first chamber is deformed, where the first chamber forms at least a portion of a coating, and where the coating is configured to be attached to an object that is configured to be inserted into an orifice.

Note that the first medium can fully encompass the second medium or a plurality of sides.

Note that the first chamber can have an angular spread about a central core, (e.g. spiral around).

Note that the dimensions of the first chamber can vary depending upon the orifice to insert. For example an object to be inserted into an ear canal with a coating attached (e.g., the first and second medium forming a first chamber) can have a maximum diameter of about 15 mm, and a maximum length of about 25 mm. If the object is to be inserted into a pipe or other orifice, the dimensions can vary appropriately so that the coating can provide some reduction of friction, or a sealing of a portion of the orifice.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A single-chamber coating of an object configured to be inserted in an ear canal, the single-chamber coating comprising:
    a first medium having a first wall and a second wall opposite the first wall forming a chamber therein, an outer surface of the first wall configured to contact a surface of the ear canal, an inner surface of the second wall including a plurality of ridges, each ridge having a greater thickness than non-ridged portions of the second wall; and
    a second medium disposed in the chamber, at least one material property of the second medium being different than the first medium,
    where the first wall is configured to apply a restorative force to the surface of the ear canal upon deformation of the chamber by the surface of the ear canal, and where the plurality of ridges are configured to direct the second medium substantially parallel to the second wall when the chamber is deformed by the surface of the ear canal.

2. The coating according to claim 1, where the second medium includes a thermally responsive polymer.

3. The coating according to claim 1, where the first medium includes a thermally responsive polymer.

4. The coating according to claim 1, where the first medium includes an electro active polymer.

5. The coating according to claim 1, where the second medium includes an electro active polymer.

6. The coating according to claim 1, where the chamber is configured to helically extend around the object.

7. The coating according to claim 1, where the single-chamber coating and the object form a sealing section, a length of the sealing section is less than 30 mm, and a diameter of the sealing section is less than 20 mm.

8. A sealing section configured to be inserted in an ear canal comprising:
    a central core; and
    a coating covering the central core, the coating comprising:
        a first medium having a first wall and a second wall opposite the first wall forming a chamber therein, an outer surface of the first wall configured to contact a surface of the ear canal, an inner surface of the second wall including a plurality of ridges, each ridge having a greater thickness than non-ridged portions of the second wall, and
        a second medium disposed in the chamber,
        where the first wall is configured to apply a restorative force to the surface of the ear canal upon deformation of the chamber by the surface of the ear canal, and where the plurality of ridges are configured to direct the second medium substantially parallel to the second wall when the chamber is deformed by the surface of the ear canal.

9. The sealing section according to claim 8, where the coating includes at least one portion such that the second medium is partitioned into a plurality of chambers.

10. The sealing section according to claim 8, where the coating is configured to helically extend around the central core.

11. The sealing section according to claim 8, where at least one of the first medium and the second medium includes a thermally responsive polymer.

12. The sealing section according to claim 8, where at least one of the first medium and the second medium includes an electro active polymer.

* * * * *